United States Patent [19]

Feld et al.

[11] Patent Number: 4,643,180
[45] Date of Patent: Feb. 17, 1987

[54] ANTIMICROBIAL DRESSING

[75] Inventors: David Feld, Arlington; Toby A. Soto, Ft. Worth, both of Tex.

[73] Assignee: Surgikos, Inc., Arlington, Tex.

[21] Appl. No.: 707,113

[22] Filed: Feb. 28, 1985

[51] Int. Cl.⁴ ............................................. A61L 15/00
[52] U.S. Cl. .................................... 128/156; 604/307
[58] Field of Search ............... 128/155, 156; 604/307; 424/28

[56] References Cited

U.S. PATENT DOCUMENTS

| 4,310,509 | 1/1982 | Berglund | 424/28 |
| 4,323,557 | 4/1982 | Rosso et al. | 424/28 |
| 4,364,949 | 12/1982 | Muntwyler et al. | 514/335 |

Primary Examiner—Stephen C. Pellegrino
Assistant Examiner—Sherri E. Vinyard
Attorney, Agent, or Firm—Michael Q. Tatlow

[57] ABSTRACT

An adhesive surgical dressing with an antimicrobial agent in the adhesive is disclosed. The antimicrobial agent is a salt of polyhexamethylene biguanide and is applied to the surface of the adhesive to a depth of not more than 50% of the thickness of the adhesive.

7 Claims, No Drawings

ANTIMICROBIAL DRESSING

The present invention relates to surgical dressings which have an adhesive surface to secure the dressings to a patient and in which the adhesive contains a salt of polyhexamethylene biguanide as a broad spectrum antimicrobial agent on the surface of the adhesive.

BACKGROUND OF THE INVENTION

The desirability of incorporating antimicrobial or antibacterial agents into different types of surgical dressings has been evident for some time. Although numerous antimicrobials are available, most of these antimicrobial agents are either not suitable for contact with human skin, or they are very difficult to incorporate into an adhesive composition.

U.S. Pat. No. 3,579,628 discloses a film dressing which contains a composition which reacts with water to generate a bacteriostatic substance.

U.S. Pat. No. 3,983,209 discloses a method of applying an antimicrobial to a wound by incorporating an antimicrobial agent into a bioerodible polymer. The polymer may be incorporated into an absorbent carrier for application to the wound.

U.S. Pat. No. 4,310,509 discloses an adhesive composition which contains a polyvinylpyrrolidone-iodine complex and which is incorporated into a solvent-based adhesive for application to a flexible backing material to be used on human skin. In order to insure that the antimicrobial will be present on the skin-contact surface of the material, the dressing is uniformly dispersed through the adhesive layer of the product.

U.S. Pat. No. 4,323,557 discloses a process incorporating a solution of an iodide and iodine into a pressure-sensitive adhesive to be used in contact with human skin.

U.S. Pat. No. 4,340,043 discloses the incorporation of uniform amounts of silver sulfadiazine as an antimicrobial into an adhesive-coated material. The skin contact adhesive is, again, a solvent-based adhesive.

Although water-based, skin contact adhesives are known, they have not been used in products containing antimicrobials. Such water-based adhesives are generally not compatible with antimicrobials as the antimicrobials are often cationic in nature. The water-based, skin-contact adhesives contain anionic surfactants as emulsifiers which are not compatible with the cationic antimicrobials. Water-based, skin-contact adhesives have an advantage in manufacturing in that they do not use environmentally undesirable solvents but use water, which may be readily removed from the adhesive when the dressing is manufactured.

The prior art antimicrobial adhesive products mentioned above also require that the antimicrobial be uniformly distributed through the entire adhesive. This requirement insures that the antimicrobial will be available on the skin-contact surface of the adhesive when the product is used.

A dressing containing an antimicrobial adhesive in which the antimicrobial is affixed on the skin-contact surface and which would not migrate would be advantageous because less antimicrobial would be required and because there would be greater assurance that the antimicrobial would be present in the skin contact surface when the product was put into use.

SUMMARY OF THE INVENTION

The present invention provides an improved process for manufacturing an antimicrobial containing adhesive dressing and provides an improved dressing in which the antimicrobial is present only in the outer, skin-contact portion of the adhesive and will not migrate prior to use and in which the antimicrobial is not inactivated by the adhesive composition.

DETAILED DESCRIPTION OF THE INVENTION

The present invention is directed to surgical dressings generally and is particularly suitable for dressings which employ substrates which are transparent and which preferably have high moisture vapor transmission rates. Dressings of this type are disclosed in U.S. Pat. No. 3,645,835. The dressings of this type are used for wound dressings as well as for incise drapes. An incise drape is used in a surgical procedure and is applied to the patient at the portion of the body where the surgical incision will be made. The surgical incision is made through the drape material. The presence of an antimicrobial in the adhesive portion of such drape prevents possible contamination of the patient from bacteria that may be present at or near the site of the incision.

The present invention may be used with any substrate normally used for making surgical dressings. The substrate may be a woven or knitted fabric, a nonwoven fabric or a plastic or polymeric film. The substrate that is preferred in the present invention is a polymeric film of polyurethane or of a copolyester which has moisture vapor transmission rates in excess of 300 grams per square meter, per 24 hours. These films are continuous in that they have no openings in the films, but the moisture vapor transmission character of the films are based on the permeability of the materials to moisture vapor. These films are generally impermeable to liquid water or to other liquids.

Adhesives that are used in the present invention are any water-based, skin-contact adhesives such as copolymers of isobutylacrylate and 2-ethylbutylacrylate containing approximately 1% or less of an anionic emulsifier. The adhesive compositions may contain polyacrylic acid thickeners and other surfactants as wetting agents. Such wetting agents could be an alkylphenoxypolyethoxyethanol. Other skin contact adhesives containing anionic emulsifiers may also be employed.

In the method of preparing the dressing of the present invention, the antimicrobial is not added to the adhesive until the adhesive has been applied to the substrate. The antimicrobial is then sprayed or otherwise applied to the exposed surface of the adhesive. When the antimicrobial is sprayed or otherwise applied on the surface of the adhesive, the cationic nature of the antimicrobial employed in the present invention interacts with the anionic surfactants in the adhesive and effectively coagulates in situ on the surface of the adhesive. When the adhesive is dried, the antimicrobial remains on the outer or skin-contact surface of the adhesive and will not substantially migrate even after long storage conditions at elevated temperatures. The depth of penetration of the antimicrobial agent into the adhesive should be limited to a depth of no more than fifty percent (50%) of the thickness of the adhesive. The preferred penetration limit is to a depth of from 10% to 25% of the thickness of the adhesive. The most preferred penetration limit is 10% of the depth of the thickness of the adhesive. When the antimicrobial agent is in the upper 10% of the thickness of the adhesive, significantly less of the antimicrobial agent is needed in the product than if the agent is uniformly distributed throughout the adhesive.

The process of the present invention generally comprises the following steps:

1. A substrate transparent film is coated with a water-based, pressure-sensitive adhesive. The coating of the adhesive may be performed by any well-known and appropriate technique such as the use of wire-wound rods, coating knives or multiple-roll coaters.

2. An aqueous solution of the cationic antimicrobial is then sprayed on the wet surface of the adhesive.

3. The antimicrobial-adhesive combination is then dried and may be laminated to a silicone-coated release paper and rewound onto a roll to be later cut to the appropriate desired size.

An alternate process, which may be used to advantage, is to dry the adhesive-coated film before the application of the cationic antimicrobial. The advantage of this dry application of the antimicrobial is that less antimicrobial is needed in the product to obtain results equivalent to that when the antimicrobial is sprayed on wet adhesive. The disadvantage of the process is that the product must be dried twice, which may add additional cost to the product.

Although numerous cationic antimicrobials are available, the present process is directed to the use of polyhexamethylene biguanide hydrochloride (hereinafter referred to as PHMB) which is the antimicrobial that is found to offer advantages in that it is a broad spectrum antimicrobial agent, and it will not cause skin irritation or be toxic at the levels in the product.

The antimicrobial is applied to the product from an aqueous solution in which the PHMB is at a concentration of from approximately 1% to 20% by weight, 4.5% being the preferred concentration. The amount of antimicrobial that is sprayed on the adhesive is controlled by the concentration of the active ingredients in the solution, the air pressure atomizing the solution, the liquid pressure, the distance between the spray head and the web which is sprayed, the spray pattern and the speed of the web. These conditions can be readily adjusted to apply a concentration of PHMB of approximately 0.05% to 2% by weight, based on the total dry weight of adhesive, on the surface of the adhesive. The preferred concentration of PHMB being from 0.45% to 1.2% by weight and the most preferred concentration is from 0.6% to 1.2% by weight.

In the following Examples the antimicrobial activity of the dressing samples is determined by the following procedure. Two inch square samples are cut from the test dressings. Individual samples are placed in a petri dish. The samples are inoculated with the test bacteria, either *Staphylococus aureus* or *Pseudomonas aeruginosa*. The surface of each sample is inoculated with about $10^6$ bacteria, and the sample is covered with a one inch glass square. The samples are neutralized at fixed times after inoculation, e.g., 0, 10, 20 or 30 minutes. The samples are cultured for 48 hours in an agar culture medium, and the surviving bacteria counted. The results are reported as a log decrease in bacteria from the "0" time to test time. For antimicrobial dressings or incise drapes, a 3 log reduction is desirable. A 3 log reduction equals a 99.9% kill of the bacteria originally present in the sample.

In some of the Examples, the antimicrobial activity of both sides of the adhesive was tested to determine the migration of the antimicrobial through the adhesive. To test the side of the sample on which the antimicrobial was sprayed, the procedure was as follows:

1. The adhesive was coated on the film portion of the dressing.
2. The antimicrobial was sprayed on the exposed surface of the adhesive.
3. The sprayed surface was covered with a release paper which was removed when the sample was tested for antimicrobial activity.

To test the side of the sample opposite the side on which the antimicrobial was sprayed, the procedure was as follows:

1. The adhesive was coated on a release paper.
2. The antimicrobial was sprayed on the surface of the adhesive.
3. The sprayed surface was covered with a plastic film.
4. The release paper was removed when the samples were tested for antimicrobial activity.

EXAMPLE I

A series of samples of products with different amounts of active antimicrobial was prepared. Each sample was made with a polyurethane film 25 microns in thickness and coated with 34 grams per square meter of an adhesive. The adhesive was a copolymer of isobutylacrylate and 2-ethylbutylacrylate having 56.3% solids. The adhesive was a water-based adhesive containing from 0.3% to 1.0% of an anionic emulsifier. The adhesive coated film was sprayed with 0.15% to 0.45% by weight based on the weight of the adhesive with a polyhexamethylene biguanide hydrochloride antimicrobial. The antimicrobial was applied to either a dry or wet adhesive. Sample A was a control with no antimicrobial. The samples were tested against *Pseudomonas aeruginosa* organisms which were present at a level of $2.51 \times 10^4$ to $2.00 \times 10^5$. The results are reported as the log change in the bacteria count.

TABLE I

Effect of PHMB Concentration on Antimicrobial Activity of Wet and Dry Adhesive vs. *Pseudomonas aeruginosa*

| Sample | Condition of Adhesive | PHMB % WT | Log Change Contact Time 10 Min. | Log Change Contact Time 30 Min. |
|---|---|---|---|---|
| A | — | 0 | −.08 | .10 |
| B | dry | .15 | −5.22* | −5.22* |
| C | dry | .30 | −5.18* | −5.18* |
| D | dry | .45 | −5.15* | −5.15* |
| E | wet | .15 | −.95 | −2.02 |
| F | wet | .30 | −.97 | −1.92 |
| G | wet | .45 | −1.80 | −2.92 |

*Total Kill

Example I shows the application of polyhexamethylene biguanide on dry adhesive yields better activity than on wet adhesive. However the dry process involves an extra drying step and reduces adhesion properties. Antimicrobial activity of samples produced by the wet adhesive process improves as the level of polyhexamethylene biguanide increases.

EXAMPLE II

The water-based antimicrobial adhesives were prepared in a manner similar to the wet process in Example I. Samples I and J have the antimicrobial at the surface of the adhesive. Sample K contains polyhexamethylene biguanide added to an adhesive dissolved in an organic solvent. Samples H and L were controls with no antimicrobial. The samples were tested against *Staphylococcus aureus* organisms which were present at a level of $2.51 \times 10^5$ to $3.63 \times 10^5$ or *Pseudomonas aeruginosa* organisms which were present at a level of $1.91 \times 10^5$ to $2.34 \times 10^5$.

TABLE II

Effect of PHMB Location on Antimicrobial Activity

| | | | Log Change | | | |
|---|---|---|---|---|---|---|
| | Adhesive | PHMB | S. aureus Contact Time | | P. aeruginosa Contact Time | |
| Sample | System | % | 10 Min. | 30 Min. | 10 Min. | 30 Min. |
| H | water | 0 | −.11 | −.32 | −.18 | −.13 |
| I | water | .6 | −4.92 | −5.40* | −5.34* | −5.34* |
| J | water | 1.2 | −5.42* | −5.42* | −5.35* | −5.35* |
| K | solvent | 5.0 | −.96 | −4.56 | −2.50 | −4.89 |
| L | solvent | 0 | −.20 | −.98 | −.18 | −.30 |

*Total Kill

Example II shows that better antimicrobial activity can be obtained with the polyhexamethylene biguanide at the surface of a water-based adhesive at levels considerably lower than with the polyhexamethylene biguanide incorporated throughout the adhesive mass.

EXAMPLE III

A series of samples in which the adhesive had been sprayed with different amounts of polyhexamethylene biguanide were prepared. Both the sprayed and unsprayed sides of unaged and aged samples were tested for antimicrobial activity. The samples were tested against *Staphylococcus aureus* organisms which were present at a level of $1.86 \times 10^5$ to $4.68 \times 10^5$. The results are shown in Tables IIIA and IIIB.

TABLE IIIA

Log Kill vs. *Staphylococcus aureus*

| | | | | One Month Aged | | | |
|---|---|---|---|---|---|---|---|
| | | | Unaged Contact Time | | Rm Temp Contact Time | | 120° F. Contact Time |
| Side | | PHMB (%) | 10 min | 30 min | 10 min | 30 min | 10 min | 30 min |
| M | **S | 0 | −0.23 | −0.48 | −0.26 | −0.26 | −0.16 | −0.32 |
| N | ***U | 0 | −0.16 | −0.22 | −0.26 | −0.35 | −0.09 | −0.41 |
| O | S | .6 | −3.53 | −5.23* | −5.40* | −5.40* | −5.28* | −5.28* |
| P | U | .6 | −0.30 | −0.44 | −0.25 | −0.57 | −0.08 | −0.32 |
| Q | S | 1.2 | −5.18* | −5.18* | −5.40* | −5.40* | −5.23* | −5.23* |
| R | U | 1.2 | −0.24 | −0.34 | −0.28 | −0.51 | −0.18 | −0.57 |

*Denotes Total Kill
**S denotes side tested was side sprayed with antimicrobial agent.
***U denotes side tested was side opposite side sprayed with antimicrobial agent.

This Example shows that there is little migration of the antimicrobial through the adhesive even when the product is aged for one month at elevated temperatures, e.g., 120° F. The samples maintained excellent antimicrobial activity on the sprayed side of the adhesive.

TABLE IIIB

Effect of Four Month Aging on Antimicrobial Activity vs. *Staphylococcus aureus*

| | | Log Change | | | |
|---|---|---|---|---|---|
| | | Room Temp. Contact Time | | 120° F. Contact Time | |
| Side | PHMB % WT | 10 Min. | 30 Min. | 10 Min. | 30 Min. |
| M S | 0 | +.03 | −.37 | +.03 | −.67 |
| N U | 0 | +.03 | −.22 | +.18 | −.54 |
| O S | .6 | −4.79 | −5.59* | −4.49 | −5.12 |
| P U | .6 | −.16 | −.47 | −.10 | −.71 |
| Q S | 1.2 | −5.27* | −5.27* | −4.59 | −5.59* |

TABLE IIIB-continued

Effect of Four Month Aging on Antimicrobial Activity vs. *Staphylococcus aureus*

| | | Log Change | | | |
|---|---|---|---|---|---|
| | | Room Temp. Contact Time | | 120° F. Contact Time | |
| Side | PHMB % WT | 10 Min. | 30 Min. | 10 Min. | 30 Min. |
| R U | 1.2 | −.14 | −.45 | +.18 | −.54 |

*Total Kill

This Example shows that there is little or no migration of the antimicrobial through the adhesive, and the product maintains good antimicrobial activity on the treated surface even when the product is aged for four months at elevated temperatures, e.g., 120° F.

Sample Q in Table IIIB was examined to determine the depth of penetration of the antimicrobial agent into the adhesive. Samples of product Q were frozen in liquid nitrogen and microtomed to obtain a cross-section of the adhesive. The adhesive layer was 30 microns in thickness. The location of the PHMB in the adhesive was determined by Scanning Transmission Electron Microscopy by scanning the sample (maintained at −100° C.) for chlorine which is present in the PHMB but not in the adhesive. The chlorine was found in the top three microns of the adhesive layer.

EXAMPLE IV

Example II was repeated using different cationic antimicrobial agents. The antimicrobial agents were BARDAC* 2250, Hyamine 3500 and chlorhexidine gluconate. A control containing no antimicrobial agent was also evaluated. Samples were tested against *Staphylococcus aureus* organisms which were present at a level of $1.95 \times 10^5$ to $2.00 \times 10^5$ and *Pseudomonas aeruginosa* organisms which were present at a level of $1.07 \times 10^5$ to $2.57 \times 10^5$. The results are shown in Table IV.

TABLE IV

Comparison of Antimicrobial Activity of Polyhexamethylene Biguanide to Other Antimicrobial Agents with Water-Based Adhesive Systems

| | | Log Change | | | |
|---|---|---|---|---|---|
| | | S. aureus Contact Time | | P. aeruginosa Contact Time | |
| Antimicrobial | % WT | 10 Min. | 30 Min. | 10 Min. | 30 Min. |
| BARDAC 2250 | 1.6 | −.24 | −.25 | −.10 | −.35 |
| Hyamine 3500 | 1.6 | −.71 | −.72 | −.79 | −.78 |
| chlorhexidine | 1.2 | — | −1.69 | — | — |
| PHMB | 1.2 | −5.42* | −5.42* | −5.35* | −5.35* |
| Adhesive only | — | −.23 | −.57 | −.07 | −.20 |

*Total Kill

This Example shows that polyhexamethylene biguanide has significantly better antimicrobial activity than other cationic agents.

We claim:

1. A surgical dressing comprising a sheet of polymeric film coated on one side with a water based adhesive, said adhesive coating being from 10 to 100 microns in thickness and having a film facing surface and a body facing surface, an antimicrobial agent deposited on the body facing surface of said adhesive, said antimicrobial agent being present in the body facing surface to a depth of from no more than 10% to 50% of the thickness of said adhesive, said antimicrobial agent comprising a salt of polyhexamethylene biguanide and being present in an amount of from 0.05% to 2% by weight based on the total weight of the adhesive.

2. The surgical dressing of claim 1 in which the concentration of the polyhexamethylene biguanide is from 0.45% to 1.2% by weight.

3. The surgical dressing of claim 1 in which the antimicrobial agent is in the upper 10% to 25% of the thickness of the adhesive.

4. The surgical dressing of claim 1 in which the polymeric film is polyurethane.

5. The process of making a surgical dressing comprising applying a water-based skin contact adhesive containing an anionic emulsifier on a substrate, applying an aqueous solution of a salt of polyhexamethylene biguanide onto the surface of the adhesive to a depth of no more than 50% of the thickness of the adhesive, said salt of polyhexamethylene biguanide being applied at a weight of 0.05% to 2% based on the dry weight of the adhesive, drying the coated substrate and covering the adhesive with a release paper.

6. The process of claim 5 in which the salt of polyhexamethylene biguanide is the chloride salt.

7. The process of claim 5 in which the adhesive is dried prior to the application of the salt of polyhexamethylene biguanide.

* * * * *